United States Patent
Wang et al.

(10) Patent No.: US 10,213,343 B2
(45) Date of Patent: Feb. 26, 2019

(54) THREE-LAYERED WOUND DRESSING AND METHOD OF MANUFACTURING THE SAME

(71) Applicant: FOSHAN UNITED MEDICAL TECHNOLOGIES, LTD., Foshan (CN)

(72) Inventors: Xiaodong Wang, Foshan (CN); Caixia Feng, Foshan (CN); Guibiao He, Foshan (CN); Jianpeng Xiao, Foshan (CN); Xiaohui Mo, Foshan (CN)

(73) Assignee: FOSHAN UNITED MEDICAL TECHNOLOGIES, LTD., Foshan (CN)

( * ) Notice: Subject to any disclaimer, the term of this patent is extended or adjusted under 35 U.S.C. 154(b) by 400 days.

(21) Appl. No.: 15/172,181

(22) Filed: Jun. 3, 2016

(65) Prior Publication Data

US 2016/0270962 A1    Sep. 22, 2016

Related U.S. Application Data

(63) Continuation-in-part of application No. PCT/CN2014/089317, filed on Oct. 23, 2014.

(30) Foreign Application Priority Data

Dec. 3, 2013 (CN) .......................... 2013 1 0642677

(51) Int. Cl.
| | |
|---|---|
| *A61F 13/00* | (2006.01) |
| *A61L 15/22* | (2006.01) |
| *A61L 15/44* | (2006.01) |
| *A61L 15/60* | (2006.01) |

(52) U.S. Cl.
CPC .. *A61F 13/00042* (2013.01); *A61F 13/00008* (2013.01); *A61F 13/00012* (2013.01); *A61F 13/00017* (2013.01); *A61F 13/00029* (2013.01); *A61F 13/00063* (2013.01); *A61F 13/00068* (2013.01); *A61F 13/00987* (2013.01); *A61L 15/225* (2013.01); *A61L 15/44* (2013.01); *A61L 15/60* (2013.01); *A61F 2210/0076* (2013.01); *A61L 2300/404* (2013.01)

(58) Field of Classification Search
CPC .......... A61F 13/00042; A61F 13/00008; A61F 13/00012; A61F 13/00017; A61F 13/00029; A61F 13/00063; A61F 13/00068; A61F 13/00987; A61L 15/225; A61L 15/44; A61L 15/60

See application file for complete search history.

(56) References Cited

U.S. PATENT DOCUMENTS

| | | | | |
|---|---|---|---|---|
| 2001/0053899 | A1* | 12/2001 | Mizutani | ........... A61F 13/51104 |
| | | | | 604/374 |
| 2004/0082925 | A1* | 4/2004 | Patel | ....................... A61L 15/44 |
| | | | | 604/289 |

* cited by examiner

*Primary Examiner* — Ophelia A Hawthorne
(74) *Attorney, Agent, or Firm* — Matthias Scholl, PC; Matthias Scholl

(57) ABSTRACT

A three-layered wound dressing, including: a first layer, a second layer, and a third layer. The first layer includes a blend of first hydrophilic fibers and first hydrophobic fibers, the second layer includes a blend of second hydrophilic fibers and second hydrophobic fibers, and the third layer includes hydrophobic fibers. The second layer is disposed between the first layer and the third layer. In use, the first layer contacts a wound.

6 Claims, 1 Drawing Sheet

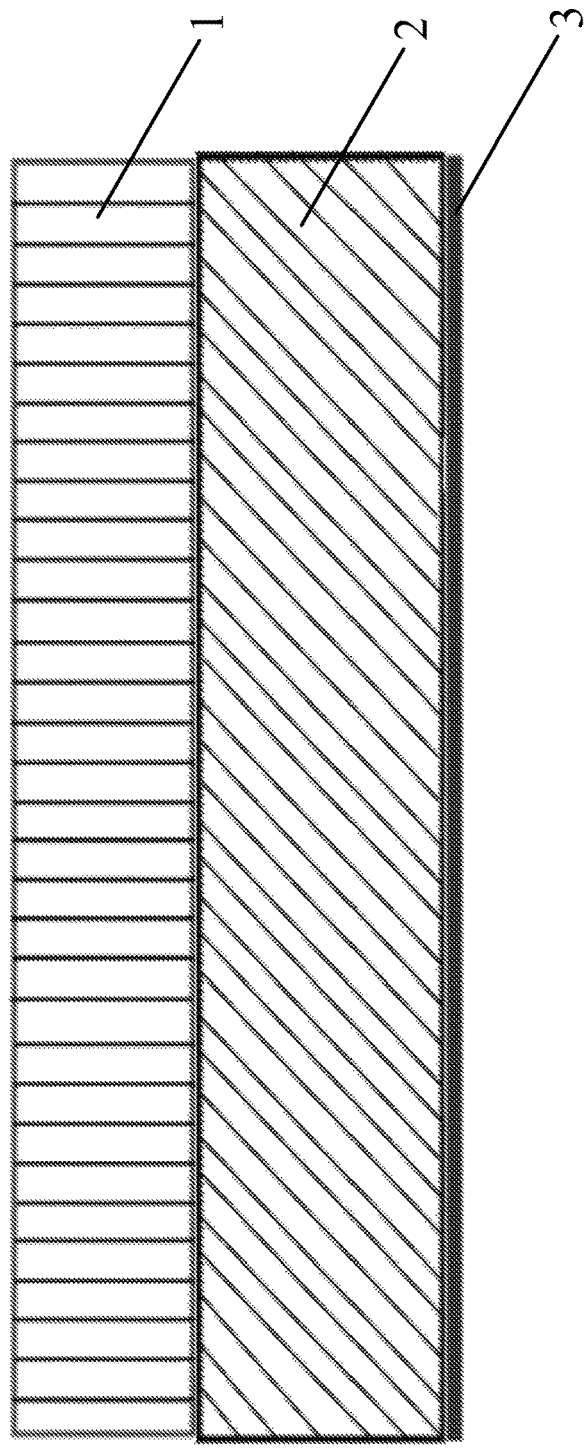

ial Patent Application No. PCT/CN2014/089317 with an international filing date of Oct. 23, 2014, designating the United States, now pending, and further claims priority benefits to Chinese Patent Application No. 201310642677.0 filed Dec. 3, 2013. The contents of all of the aforementioned applications, including any intervening amendments thereto, are incorporated herein by reference.

THREE-LAYERED WOUND DRESSING AND METHOD OF MANUFACTURING THE SAME

CROSS-REFERENCE TO RELATED APPLICATIONS

This application is a continuation-in-part of International Patent Application No. PCT/CN2014/089317 with an international filing date of Oct. 23, 2014, designating the United States, now pending, and further claims priority benefits to Chinese Patent Application No. 201310642677.0 filed Dec. 3, 2013. The contents of all of the aforementioned applications, including any intervening amendments thereto, are incorporated herein by reference.

BACKGROUND OF THE INVENTION

Field of the Invention

This invention relates to a three-layered wound dressing and a method of manufacturing the same.

Description of the Related Art

Conventional wound dressings do not absorb wound exudate quickly enough, and when the exudate from a wound is heavy, the absorbed fluid tends to spread over to non-infected areas, thus causing lateral wicking of the fluid. As a result, the healthy skin is often macerated and damaged by the wound fluid.

SUMMARY OF THE INVENTION

In view of the above-described problems, it is one objective of the invention to provide a three-layered wound dressing. The dressing comprises three layers, i.e., a first layer, a second layer and a third layer, wherein, when used in the wound management, the first layer contacts the wound (also referred to as wound contact layer). The second layer is the middle layer (also referred to as the absorbent layer, and the third layer is the outer layer. The first layer comprises first hydrophilic fibers and first hydrophobic fibers, the middle layer is a nonwoven comprising second hydrophilic fibers and second hydrophobic fibers, and the third layer is a nonwoven of third hydrophobic fibers.

The role of the first layer is to absorb and transfer quickly the wound fluid to the middle absorbent layer. This transfer is almost vertical, i.e. with no or very little lateral transfer, thus ensuring the majority of the wound fluid is transferred to the middle absorbent layer, not to the surrounding areas. The middle absorbent layer is designed to absorb and to retain the wound fluid. The third layer can be a colored fabric so to differentiate it from the first layer. Because the third layer is a hydrophobic material, it can help keep the wound fluid absorbed by the second layer within the dressing.

According to the invention, the first layer contains 75% or less by weight (of the first layer) hydrophilic fibers and hydrophobic fibers. The proportion of hydrophilic fiber is preferably 60% or less, most preferably 50% by weight. This is different from the design theory of some traditional dressings where the first layer is made up with 100% hydrophilic fibers. With 100% hydrophilic fiber, it is difficult to avoid lateral wicking and maceration of surrounding healthy skin. The invention has unexpectedly found that by adding a certain percent of hydrophobic fibers to the dressing, the lateral wicking can be reduced or prevented.

According to the invention, the first hydrophilic fibers in the first layer is selected from: viscose fibers, absorbent acrylic fibers, absorbent polypropylene fibers, Lyocell fibers, alginate fibers, chitosan fibers, carboxymethyl cellulose fibers (CMC), carboxy ethyl cellulose (CEC) fibers, acylated chitosan fibers, carboxymethyl chitosan fibers, or a mixture thereof. The first hydrophobic fibers in the first layer can be selected from polypropylene fibers, polyester fibers, nylon (Polyamide) fibers, polyethylene fibers, hydrophobic chitosan fibers, bi-component fibers, or a mixture thereof.

Amongst the above hydrophilic fibers, the viscose, lyocell, alginate, carboxymethyl cellulose, carboxy ethyl cellulose, acylated chitosan fibers are all well know. Chitosan fibers are normally hydrophobic, but can be made hydrophilic by adding certain surfactants or by other modifications. The same apples to acrylic and polypropylene fibers.

The difference between hydrophilic and hydrophobic fibers can be seen by a simple sink test. When the fibers are placed onto a water surface, the hydrophilic fibers will sink but the hydrophobic will not. This test can be described in details as follow:

Take a beaker with 200 mL of distilled water;
Take a fixed amount of fiber e.g. 1 gram;
Make fibers into a knot so they are not spread over on the water, then place it into the beaker;
If the fiber knot sinks within 5 seconds, it is hydrophilic otherwise hydrophobic.

Hydrophilic and hydrophobic fibers can be mixed at a certain ratio at carding stage, then opened together, followed by carding and crosslapping which will make further blending. The first layer can be a needle punched nonwoven. If the hydrophobic fibers contain bi-component fibers, the fabric can also be made by passing the web into a high temperature oven or a pair of hot rollers which will make the bi-component fiber partially melt causing the interlink between the bi-component fibers.

The first layer can be bonded with the other two layers by needle punching, it can also be made by adhesive or heat laminating. This is very much dependent on the handling requirement of the finished dressing and whether the dressing contains fibers with a low melting point. If the dressing contains fibers with a low melting point, the lamination can be made with any of three methods (needling, heat or adhesive). If the dressing dos not contain fibers with low melt point, the lamination can only be made with needling and adhesive. In general, the heat lamination and adhesive lamination will make the finished dressing feel rigid and hard (harsh handling). If softness is one of the key requirements, needle punching is the best way for lamination of three layers.

It is also possible to laminate the first layer directly onto the other two layers after blending, opening and carding.

According to the invention, the weight of the first layer is between 50-500 g/m$^2$ (gsm), preferably 80-450 gsm, more preferably 100-400 gsm.

According to the invention, the second layer also contains hydrophilic and hydrophobic layer. The percentage of hydrophobic fibers shall be 75% or less (by weight of the second layer), preferably 60% or less, most preferably 50% or less. The main objective of the second layer is to absorb wound exudates transferred from the first layer, therefore one of the key characteristics of the invention is the high absorbency of the second layer. The ratio between the hydrophilic fibers to the hydrophobic fibers in the second layer shall be selected according to the requirements of the finished dressing. With some hydrophobic fibers in the second layer, it can reduce some gelling fibers forming gel blocks which may prevent the spreading of the fluid along the second layer thus limiting the absorption capacity of the layer. However too much hydrophobic fiber will reduce the absorption capacity of the second layer.

According to the invention, the second hydrophilic fibers on the second layer can be selected from absorbent chitosan fibers, viscose fibers, Lyocell fibers, alginate fibers, carboxymethyl cellulose fibers, carboxy ethyl cellulose fibers, acylated chitosan fibers, carboxymethyl chitosan fibers, cross-linked acrylates copolymer super absorbent fibers, wood pump, or a mixture thereof. The second hydrophobic fibers can be selected from polypropylene fibers, polyester fibers, nylon (Polyamide) fibers, polyethylene fibers, hydrophobic chitosan fibers, bi-component fibers, or a mixture thereof.

The above hydrophilic fibers have their own characteristics such as carboxymethyl cellulose fibers, carboxy ethyl cellulose fibers, acylated chitosan fibers, carboxymethyl chitosan fibers and cross-linked acrylates copolymer super absorbent fibers (SAF) are all very absorbent. The alginate fibers can release calcium ions, the chitosan fibers are bacteriostatic, and the viscose fibers have high wet strength.

The second layer can be made into fabric first before laminating to the layers. It can also be made into web then laminated to the third layer directly.

According to the invention, the weight of the second layer shall be between 80-500 gsm, preferably 100-450 gsm, most preferably 100-400 gsm.

According to the invention, the third layer is made with third hydrophobic fibers and can be selected from polypropylene fibers, polyester fibers, nylon (Polyamide) fibers, polyethylene fibers, hydrophobic chitosan fibers, bi-component fibers. The bi-component fibers in the invention can be PE/PP fibers, or Nylon (Polyamide)/PE, or PET/Nylon (Polyamide), or a mixture thereof.

Most hydrophobic fibers are made with hot melt method, therefore the third layer of the invention is usually made with hot melt spinning or spunbond methods. For those fibers that are not made by hot melt method, it can also be made with hydro entanglement method.

According to the invention, the weight of the third layer shall be between 10-100 gsm, preferably 10-80 gsm, more preferably 10-60 gsm.

According to the invention, the first layer, second layer and the third layer can be colored or not colored (original color of the fiber). In general, the third layer is colored and the first layer is not colored so that the end user (such as nurse or doctor) can tell the third layer and the first layer. The second layer is usually not colored.

According to the invention, the dressing of the invention can be made into antimicrobial by adding some antimicrobial agents such as silver, silver compound, silver complex, Polyhexamethylene biguanide (PHMB) and honey etc. can be added to hydrophilic fibers and/or hydrophobic fibers in the first layer and/or second layer.

The invention does not limit the method of adding antimicrobial agents. These methods include one of the following three steps:

1) Adding antimicrobial agents such as silver nitrate, silver chloride, silver carbonate, silver sodium zirconium hydrogen phosphate into polymer solution of fiber spinning (dope), thus making the fibers antimicrobial. This method can make the silver content in the fiber between 0.001%-10%.

2) Spraying the silver solution (such as nano silver solution) onto the fiber surface. This method can make the silver content of the fiber between 0.01%-2%.

3) Coating the silver onto the fiber surface. This method can make the silver content of the fiber between 0.1%-25%.

The invention also discloses a method of manufacturing the above dressing. The main elements of the method comprise one of the following steps:

1. Manufacturing the first layer, second layer and the third layer separately using hot melt, needle punch or hydro entanglement methods. Then by heat lamination or needle punching or adhesive laminate the first layer, second layer and the third layer together, followed by slitting, cutting, packaging and sterilization.

2. Manufacturing the first layer and the second layer separately using hot melt, needle punch or hydro entanglement methods. Then by heat lamination or needle punching or adhesive laminate the first layer and the second layer together, then manufacture the third layer directly onto the laminated layers (wound contact and second layers), followed by slitting, cutting, packaging and sterilization.

3. Manufacturing the second layer and the third layer separately using hot melt, needle punch or hydro entanglement methods. Then by heat lamination or needle punching or adhesive laminate the second layer and the third layer together, then manufacture the first layer directly onto the laminated layers (middle and third layers), followed by slitting, cutting, packaging and sterilization.

The invention also discloses an application of the above products for the management of chronic wounds.

The wound dressing in the invention can transfer the fluid vertically (other than laterally). When the first layer absorbs the fluid, it can transfer the wound exudates into the second layer quickly and keep the first layer relevantly dry, preventing the maceration of the surrounding healthy skin. The dressing can be used for the management of chronic wounds, particularly of the heavily exudating wounds.

BRIEF DESCRIPTION OF THE DRAWINGS

The invention is described hereinbelow with reference to accompanying drawings, in which the sole FIGURE is a schematic diagram of a three-layered wound dressing according to one embodiment of the invention.

In the drawings, the following reference numbers are used: 1. First layer; 2. Second layer; and 3. Third layer.

DETAILED DESCRIPTION OF THE EMBODIMENTS

To further illustrate the invention, experiments detailing a three-layered wound dressing and a method of manufacturing the same are described below. It should be noted that the following examples are intended to describe and not to limit the invention.

Example 1

The three layers are made separately in the following method.

First layer: contains 75% by weight of polypropylene fibers (PP), fiber linear density 2.0 dtex, fiber length 38 mm; and 25% of alginate fibers, fiber linear density 2.5 dtex, fiber length 75 mm. The above two fibers are mixed evenly and then processed by opening, carding, crosslapping and needle punching. The needling density is 80/cm$^2$. The finished fabric has a weight of 310 gsm.

The second layer: contains 35% by weight of cross-linked acrylates copolymer super absorbent fibers (SAF), fiber linear density 2.7 dtex, length 10 mm; 50% by weight of wood pump, fiber linear density 2.5 dtex, length 10 mm; and 15% by weight of PP/PE bi-component fibers, fiber linear density 2.0 dtex, length 10 mm. All three fibers are blended by hands or by an opener evenly, followed by opening and air laying and finally hot oven to form the fabric. The weight of the fabric is 180 gsm.

The third layer: PP spun bond fabric, weight 30 gsm, beige color.

The heat lamination method is used to combine the second layer and the third layer, then the needle punch method is used to laminate the first layer onto the above laminated layers.

Samples are cut into 10×10 cm, then packed into pouches, and sterilized by gamma irradiation. The finished dressing has a weight of 520 gsm, and an absorbency of 44 g/100 cm$^2$.

Example 2

The three layers are made in the following method.

First layer: contains 50% by weight of hydrophobic chitosan fibers, fiber linear density 2.2 dtex, fiber length 51 mm; and 50% by weight of viscose fibers, fiber linear density 1.7 dtex, fiber length 51 mm. The above two fibers are mixed evenly and then processed by opening, carding, crosslapping and needle punching. The needling density is 100/cm$^2$. The weight of the finished fabric is 100 gsm.

The second layer: contains 35% by weight of SAF fibers, fiber linear density 2.7 dtex, length 25 mm; 15% by weight of viscose fibers, fiber linear density 2.5 dtex, length 51 mm; and 50% by weight of PP fibers, fiber linear density 2.0 dtex, length 38 mm. All three fibers are blended evenly, followed by opening, carding, cross-lapping and needle punched into nonwoven fabric. The needling density is 100/cm$^2$. The weight of the fabric is 150 gsm.

The third layer: hydro entangled Lyocell nonwoven, weight 40 gsm, white color.

The first layer, second layer and the third layer are placed onto the conveyor belt of the cross-lapping machine, and fed into the needle loom and needled into laminated fabric. The needle density is 150/cm$^2$.

Samples are cut into 10×10 cm, then packed into pouches and sterilized by EtO. The finished dressing has a weight of 290 gsm, absorbency 47 g/100 cm$^2$.

Example 3

The three layers are made in the following method.

First layer: contains 10% by weight of hydrophobic chitosan fibers, fiber linear density 2.2 dtex, fiber length 51 mm; and 75% by weight of viscose fibers, fiber linear density 1.7 dtex, fiber length 51 mm; and 15% by weight of PP/PE bi-component fibers, fiber linear density 2.0 dtex, length 38 mm. The above three fibers are mixed evenly and then processed by opening, carding, and then heat processing to form the fabric. The weight of the finished fabric is 300 gsm.

The second layer: contains 20% by weight of alginate fibers, fiber linear density 2.5 dtex, length 75 mm; 50% by weight of Lyocell fibers, fiber linear density 1.7 dtex, length 51 mm; and 30% by weight of PP/PE bi-component fibers, fiber linear density 2.0 dtex, length 38 mm. All three fibers are blended evenly, followed by opening, carding, and heat process to form the nonwoven fabric. The weight of the fabric is 150 gsm.

The third layer: PP spun bond fabric, weight 30 gsm, pink color.

The first layer, second layer and the third layer are placed together into a heat process to laminate the three layers.

Samples are cut into 10×10 cm, then packed into pouches and sterilized by EtO. The finished dressing has a weight of 480 gsm, absorbency 35 g/100 cm$^2$.

Example 4

The three layers are made in the following method.

First layer: contains 70% by weight of polypropylene fibers (PP), fiber linear density 2.0 dtex, fiber length 38 mm; and 30% of Lyocell fibers, fiber linear density 1.7 dtex, fiber length 51 mm. The above two fibers are mixed evenly and then processed by opening, carding and crosslapping.

The second layer: contains 25% by weight of CMC fibers, fiber linear density 2.2 dtex, length 50 mm; 75% by weight of PET fibers, fiber linear density 1.4 dtex, length 51 mm. All two fibers are blended evenly, followed by opening, carding, crosslapping and needle punching. The weight of the needled fabric is 200 gsm.

The third layer: PP spun bond fabric, weight 30 gsm, beige color.

During the process to manufacture the first layer, the second layer and the third layer are placed in order (third layer at the bottom) onto the conveyor belt of the cross lapping machine, then fed into the needling looms. The needling density was 150/cm$^2$. The needling has pushed the fibers of the first layer through the second layer and then into the third layer, thus laminating the three layers together.

Samples are cut into 10×10 cm, then packed into pouches, and sterilized by gamma irradiation. The finished dressing has a weight of 430 gsm, absorbency 39 g/100 cm$^2$.

Example 5

The three layers are made in the following method.

First layer: contains 75% by weight of polypropylene fibers (PP), fiber linear density 2.0 dtex, fiber length 38 mm; and 25% of silver alginate fibers, silver content 2.1%, fiber linear density 2.6 dtex, fiber length 75 mm. The above two fibers are mixed evenly and then processed by opening, carding, crosslapping and needle punching. The needling density is 80/cm$^2$. The weight of the finished fabric is 300 gsm.

The second layer: contains 25% by weight of SAF fibers, fiber linear density 2.7 dtex, length 38 mm; 75% by weight of PET fibers, fiber linear density 1.4 dtex, length 51 mm. The two fibers are blended evenly, followed by opening, carding, cross-lapping and needle punched into nonwoven fabric. The weight of the fabric is 200 gsm.

The third layer: PP spun bond fabric, weight 30 gsm, beige color.

The first layer, second layer and the third layer are placed onto the conveyor belt of the cross-lapping machine, and fed into the needle loom and needled into laminated fabric. The needle density is 150/cm$^2$.

Samples are cut into 10×10 cm, then packed into pouches and sterilized by Gamma. The finished dressing has a weight of 530 gsm, absorbency 42 g/100 cm$^2$.

Example 6

The three layers are made in the following method.

First layer: contains 70% by weight of polypropylene fibers (PP), fiber linear density 2.0 dtex, fiber length 38 mm; and 30% of Lyocell fibers, fiber linear density 1.7 dtex, fiber length 51 mm. The above two fibers are mixed evenly and then processed by opening, carding, crosslapping and needle punching. The needling density is 80/cm², the weight of the finished layer is 100 gsm.

The second layer: contains 40% by weight of silver alginate fibers, silver content 2.1%, fiber linear density 2.6 dtex, length 75 mm; 60% by weight of PET fibers, fiber linear density 1.4 dtex, length 51 mm. All two fibers are blended evenly, followed by opening, carding, crosslapping and needle punching. The weight of the needled fabric is 100 gsm.

The third layer: PP spun bond fabric, weight 30 gsm, beige color.

The first layer, second layer and the third layer are placed onto the conveyor belt of the cross-lapping machine, and fed into the needle loom and needled into laminated fabric. The needle density is 150/cm².

Samples are cut into 10×10 cm, then packed into pouches, and sterilized by gamma irradiation. The finished dressing has a weight of 230 gsm, absorbency 32 g/100 cm².

Example 7

The first layer and the second layer are the same as the ones from Example 6, feed both fabrics into the needle loom to laminate by needling. The laminated fabric is then placed before the calender rollers of the polypropylene spun bond line, ensuring the second layer facing the income polypropylene material so that spun bond polypropylene is laid onto the second layer, and all three layers are fed into the calender rollers together, thus making the spun bond polypropylene laminated onto the second layer/first layer.

Samples are cut into 10×10 cm, then packed into pouches, and sterilized by gamma irradiation. The finished dressing has a weight of 230 gsm, absorbency 30 g/100 cm².

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method of manufacturing a three-layered wound dressing, the three-layered wound dressing comprising a first layer, a second layer, and a third layer; the first layer comprising a blend of first hydrophilic fibers and first hydrophobic fibers; the second layer comprising a blend of second hydrophilic fibers and second hydrophobic fibers; and the third layer comprising hydrophobic fibers; the second layer being disposed between the first layer and the third layer; and the first layer being adapted to contact a wound; the method comprising one of the following three steps:

1) manufacturing the first layer, the second layer and the third layer separately using a heat binding method, or a needle punching method or a hydro entanglement method; then laminating three layers together by heat bonding, or needle punching or chemical bonding, followed by cutting, packing and sterilization;

2) manufacturing the first layer, the second layer and the third layer separately using a heat binding method, or a needle punching method or a hydro entanglement method; laminating the first layer and the second layer together by heat bonding, or needle punching or chemical bonding; and then manufacturing the third layer onto the laminated first/second layer directly, followed by cutting, packing and sterilization; and 3) manufacturing the second layer and the third layer separately using a heat binding method, or a needle punching method or a hydro entanglement method; laminating the second layer and the third layer together by heat bonding, or needle punching or chemical bonding; and manufacturing the first layer onto the laminated second layer/third layer directly, followed by cutting, packing and sterilization.

2. The method of claim 1, wherein the first layer comprises a blend of the first hydrophilic fibers and the first hydrophobic fibers, and a percentage of the first hydrophilic fibers is 75% or less by weight of the first layer.

3. The method of claim 1, wherein the second layer comprises the second hydrophilic fibers and the second hydrophobic fibers, and a percentage of the second hydrophobic fibers is, by the weight of the second layer, 75% or less.

4. The method of claim 1, wherein the third hydrophobic fibers of the third layer are selected from polypropylene (PP) fibers, polyester (PET) fibers, Polyamide (PA) fibers, polyethylene (PE) fibers, hydrophobic chitosan fibers, PP/PE bi-component fibers, PA/PE bi-component fibers, PET/PA bi-component fibers, or a mixture thereof.

5. The method of claim 1, wherein a weight of the first layer is between 50-500 gram per square meter (gsm), and/or a weight of the second layer is between 80-500 gsm, and/or a weight of the third layer is between 51-100 gsm.

6. The method of claim 1, wherein the hydrophilic fibers and/or hydrophobic fibers of the first layer and/or the second layer comprises antimicrobial agents selected from the group consisting of silver, silver compound, silver complex, Polyhexamethylene biguanide (PHMB) and honey.

* * * * *